(12) United States Patent
Zhang

(10) Patent No.: US 8,915,942 B2
(45) Date of Patent: Dec. 23, 2014

(54) SKIN WOUND CLOSURE APPARATUS

(75) Inventor: Shengping Zhang, Chengdu (CN)

(73) Assignee: Sichuan Lichen Medical & Pharmaceutical Technology Co., Ltd., Chengdu (CN)

( * ) Notice: Subject to any disclaimer, the term of this patent is extended or adjusted under 35 U.S.C. 154(b) by 112 days.

(21) Appl. No.: 13/699,411

(22) PCT Filed: Jun. 1, 2011

(86) PCT No.: PCT/CN2011/075072
§ 371 (c)(1),
(2), (4) Date: Nov. 21, 2012

(87) PCT Pub. No.: WO2011/150847
PCT Pub. Date: Dec. 8, 2011

(65) Prior Publication Data
US 2013/0072969 A1  Mar. 21, 2013

(30) Foreign Application Priority Data
Jun. 2, 2010 (CN) .......................... 2010 1 0189559

(51) Int. Cl.
*A61B 17/08* (2006.01)
*A61B 17/00* (2006.01)

(52) U.S. Cl.
CPC .............. *A61B 17/08* (2013.01); *A61B 17/085* (2013.01); *A61B 2017/00477* (2013.01); *A61B 2017/086* (2013.01)
USPC ........................................................ 606/216

(58) Field of Classification Search
USPC ........... 128/849, 855; 606/213–218, 221, 233
See application file for complete search history.

(56) References Cited

U.S. PATENT DOCUMENTS

| 2,191,228 A * | 2/1940 | Dowd .............................. 24/170 |
| 3,971,384 A | 7/1976 | Hasson |
| 2005/0021083 A1* | 1/2005 | Lebner .......................... 606/216 |

FOREIGN PATENT DOCUMENTS

| CN | 2885137 Y | 4/2007 |
| CN | 101112326 A | 1/2008 |

(Continued)

OTHER PUBLICATIONS

International Search Report for PCT/CN2011/075072 dated Sep. 8, 2011.

*Primary Examiner* — Ashley Fishback
(74) *Attorney, Agent, or Firm* — Caesar, Rivise, Bernstein, Cohen & Pokotilow, Ltd.

(57) ABSTRACT

The invention discloses a skin wound closure device capable of promoting skin wound healing and characterized by being capable of randomly adjusting stitching force for a wound. The skin wound closure device includes a support structure respectively arranged at both sides of a skin wound, at least one locking device is arranged above the support structure, the locking device includes a locking bar and a locking buckle arranged on the support structure, the locking bar is movably connected within the locking buckle, and a locking member is arranged on the locking buckle and can lock or loosely fit the locking bar in the locking buckle. Arrangement of the locking member allows doctors to loosely fit the locking bar in the locking buckle by controlling the locking member, randomly move the support structure and the locking device towards the direction close to the skin wound or the direction away from the skin wound, and lock the locking bar in the locking buckle by the locking member after proper movement, thus achieving the purpose of randomly adjusting the stitching force for the skin wound. The skin wound closure device is suitable for widespread application to healing treatment of skin wounds.

20 Claims, 2 Drawing Sheets

(56) References Cited

FOREIGN PATENT DOCUMENTS

| | | |
|---|---|---|
| CN | 101828939 A | 9/2010 |
| CN | 101843507 A | 9/2010 |
| CN | 201683934 U | 12/2010 |
| CN | 201683935 U | 12/2010 |
| WO | 2009066116 A1 | 5/2009 |

* cited by examiner

SKIN WOUND CLOSURE APPARATUS

FIELD OF THE INVENTION

The invention relates to a medical device applied to skin wound closure, and in particular to a skin wound closure device capable of promoting skin wound healing.

DESCRIPTION OF THE RELATED ART

At present, skin wound closure devices such as skin zippers can avoid the following shortcomings of traditional methods for stitching skin wounds by needle and thread: formation of new skin wounds, allergy to suture line, retention of foreign material, infectibility and "centipede feet"-like scar on healed wounds. Invention Patent Examination Specification of application Ser. No. 8,7108,125 entitled "Wound Closure Apparatus" discloses such a medical device for skin wounds. However, such wound closure apparatus causes additional shortcomings due to whole wound closure in use, that is, it is difficult for doctors to operate and check for flat face-to-face closure of skin wound edges, wound healing situations can not be observed, it is very inconvenient for wound breathability and discharge of wound drainage as dried blood and wound secretion condense below closed surfaces, and requirements for wound cleaning and dressing change can not be met. U.S Pat. No. 3,117,364.0 solves the shortcomings, however, the stitching force for locking wounds can be adjusted only in one direction (the stitching force can be increased without doubt) as principles of a ratchet wheel is used in the patent, and the urgent needs of doctors for random adjustment to increase or decrease the stitching force applied to wounds can not be met during wound stitching and wound healing (e.g. when wounds have to be drained or placed with instruments).

SUMMARY OF THE INVENTION

The technical problem to be solved by the invention is to provide a skin wound closure device capable of randomly adjusting stitching force for a wound.

A technical solution for solving the technical problem of the invention is a skin wound closure device, comprising a support structure respectively arranged at both sides of a skin wound, at least one locking device is arranged above the support structure, the locking device comprises a locking bar and a locking buckle arranged on the support structure, the locking bar is movably connected within the locking buckle, and a locking member is arranged on the locking buckle and can lock or loosely fit the locking bar in the locking buckle.

Furthermore, a through hole passing through and sheathing the locking bar is arranged in the locking buckle, and the locking member is of a rolling element arranged between an upper surface of the locking bar and a top wall of the through hole.

Furthermore, a chute is arranged at the top wall of the through hole, the rolling element is arranged in the chute, and diameter of the rolling element is greater than or equal to height from an inside top wall of the chute to the upper surface of the locking bar, and smaller than height from an outside top wall of the chute to the upper surface of the locking bar.

Furthermore, a bar through hole in communication with the chute is arranged on the top of the locking buckle.

Furthermore, a projection for increasing friction force is arranged at the upper surface of the locking bar.

Furthermore, the support structure respectively located at both sides of the skin wound comprises a support belt and a base belt arranged on an upper surface of the support belt, and the locking buckle is fixedly arranged on the base belt.

Furthermore, the base belt is arranged at an inside edge of the upper surface of the support belt, and the support belt and the inside edge of the base belt are of an arc surface.

Furthermore, a hypoallergenic adhesive is coated to a lower surface of the support belt.

As one of preferred embodiments, the support structure at each side is provided with the locking buckle, and two ends of the locking bar are movably connected with the locking buckle at both sides of the skin wound.

As another preferred embodiment, the locking buckle is only arranged on the support structure at one side of the skin wound, one end of the locking bar is movably connected with the locking buckle, and the other end thereof is fixedly connected to the support structure at the other side.

The beneficial effects of the invention are as follows: arrangement of the locking member allows doctors to loosely fit the locking bar in the locking buckle by controlling the locking member, randomly move the support structure and the locking device towards the direction close to the skin wound or the direction away from the skin wound, and lock the locking bar in the locking buckle by the locking member after proper movement, thus achieving the purpose of randomly adjusting the stitching force for the skin wound; and the non-closed structure connected with the locking bar is convenient for breathability, drainage and dressing change of the skin wound, can help observe face-to-face closure and healing situations of skin edges of the skin wound under direct vision at any time, and is suitable for widespread application to healing treatment of skin wounds.

Figure 1:
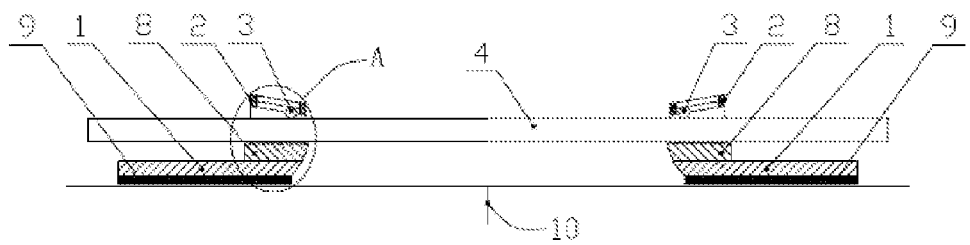
FIG. 1 is a structural diagram of an embodiment of the invention.

Marks in the figures are as follows: support belt 1, locking buckle 2, locking member 3, locking bar 4, through hole 5, chute 6, bar through hole 7, base belt 8, hypoallergenic adhesive 9 and skin wound 10.

DESCRIPTION OF THE PREFERRED EMBODIMENTS

The invention will be further described in detail in combination with accompanying drawings and embodiments.

As shown in FIG. 1 to FIG. 4, the skin wound closure device of the invention comprises a support structure respectively arranged at both sides of a skin wound 10, at least one locking device is arranged above the support structure, the locking device comprises a locking bar 4 and a locking buckle 2 arranged on the support structure, the locking bar 4 is movably connected within the locking buckle 2, and a locking member 3 is arranged on the locking buckle 2 and can lock or loosely fit the locking bar 4 in the locking buckle 2. The support structure is arranged at both sides of an animal or human skin wound 10 in operation. When stitching force for the skin wound 10 has to be increased, the locking bar 4 is loosely fit in the locking buckle 2 by operating the locking member 3, and then the support structure and the locking device are moved inwards (towards the direction of the skin wound 10) to increase the stitching force for the skin wound 10 for closure and face-to-face closure of skin edges at both sides of the skin wound 10, then the locking member 3 is operated to compress the locking bar 4 in the locking buckle 2 so as to lock and maintain moderate stitching tension for face-to-face closed skin edges at both sides to promote natural healing of the skin wound 10; and the support structure and the locking device are moved outwards (away from the direction of the skin wound 10) to decrease the stitching force when the locking bar 4 is loosely fit in the locking buckle 2. Arrangement of the locking member 3 allows doctors to loosely fit the locking bar 4 in the locking buckle 2 by controlling the locking member 3, randomly move the support structure and the locking device towards the direction close to the skin wound 10 or the direction away from the skin wound 10, and lock the locking bar 4 in the locking buckle 2 by the locking member 3 after proper movement, thus achieving the purpose of randomly adjusting the stitching force for the skin wound 10. The non-closed structure connected with the locking bar 4 is convenient for breathability, drainage and dressing change of the skin wound 10, and can help observe face-to-face closure and healing situations of skin edges of the skin wound 10 under direct vision. It is better to provide multiple locking devices so as to achieve better closure effect for the skin wound 10.

In the embodiment, the form of movably connecting the locking bar 4 in the locking buckle 2 can be arrangement of a chute adapted to the locking bar 4 on the locking buckle 2 so as to slidably fit the locking bar 4 in the chute; the locking member 3 can be of a screw, and the locking bar 4 can be locked or unfastened by screwing the screw in the forward or reverse direction when the locking member 3 is of a screw. As a preferred embodiment, a through hole 5 passing through and sheathing the locking bar 4 is arranged in the locking buckle 2, and the locking member 3 is of a rolling element arranged between an upper surface of the locking bar 4 and a top wall of the through hole 5. The rolling element can be of a circular steel ball or a rolling column When the rolling element is used as the locking member 3, the locking bar 4 can be locked or unfastened only by controlling rolling of the rolling element. For example, the locking bar 4 can be in a loose state in the through hole 5 by rolling the rolling element out of the through hole 5, and the locking bar 4 can be locked by placing the rolling element in the through hole 5. For convenient control of the rolling element by doctors, as a preferred embodiment, a chute 6 is arranged at a top wall of the through hole 5, the rolling element is arranged in the chute 6, and diameter of the rolling element is greater than or equal to height from an inside top wall of the chute 6 to the upper surface of the locking bar 4, and smaller than height from an outside top wall of the chute 6 to the upper surface of the locking bar 4. Inside described herein refers to the side close to the skin wound 10, and outside refers to the side away from the skin wound 10. By arrangement of the chute 6, and as diameter of the rolling element is greater than or equal to the height from the inside top wall of the chute 6 to the upper surface of the locking bar 4, and smaller than the height from the outside top wall of the chute 6 to the upper surface of the locking bar 4, the bottom of the rolling element can leave the upper surface of the locking bar 4 so as to cause the locking bar 4 to be in a loose state in the through hole 5 when the rolling element is moved outwards as the diameter of the rolling element is smaller than height from the outside top wall of the chute 6 to the upper surface of the locking bar 4, that is, the support structure and the locking device respectively arranged at both sides of the skin wound 10 can be freely moved to adjust the stitching force for the skin wound 10; and the rolling element can compress the locking bar 4 so as to close the skin wound 10 when the rolling element is moved inwards as the diameter of the rolling element is greater than or equal to the height from the inside top wall of the chute 6 to the upper surface of the locking bar 4. In the adjustment method, the locking bar 4 can be locked or unfastened without moving the rolling element out of the through hole 5.

For convenient control of the rolling element by doctors, a bar through hole 7 in communication with the chute 6 is arranged on the top of the locking buckle 2. The bar through hole 7 can be designed as per size of forceps or other tools or supporting special tools used by doctors in operations, so that doctors can control the rolling element to roll outwards or inwards in the chute 6 through the bar through hole 7, thus randomly controlling compression or loosening effects of the rolling element on the locking bar 4.

In the embodiment, a projection for increasing friction force is arranged at the upper surface of the locking bar 4 to prevent slipping when the rolling element locks the locking bar 4. Arrangement of the projection can increase friction force between the locking bar 4 and the rolling element, thus preventing slipping during locking and improving reliability of closure of the skin wound 10.

In the embodiment, the support structure respectively located at both sides of the skin wound 10 can be of any structure for effective support and connection of the locking buckle 2, for example, a plate can be used for support and connection of the locking buckle 2. As a preferred embodiment, the support structure respectively located at both sides of the skin wound 10 comprise a support belt 1 and a base belt 8 arranged on an upper surface of the support belt 1, and the locking buckle 2 is fixedly arranged on the base belt 8. The support belt 1 can effectively contact the skin, and arrangement of the base belt 8 can greatly improve stress reliability of the locking buckle 2, thus being capable of improving service life of the whole device. The support belt 1 can be made of polyamide, polyester fabric or bandage cloth with longitudinal hypoelasticity and transverse stretchability, and the base belt 8 and the locking device can be made of polyamide, polyester, polyene, stainless steel or other metallic materials.

In order to improve healing effect of the skin wound 10, the base belt 8 is arranged at an inside edge of the upper surface of the support belt 1, and the support belt 1 and the inside edge of the base belt 8 are of an arc surface. As shown in FIG. 1, arrangement of the arc surface can press skin edge of the wound during closure of the skin wound 10, thus causing slight ectropion of the wound, and being capable of promoting healing of the skin wound 10 and ensuring good appearance of the healed skin wound 10.

In order to prevent damage from the skin wound closure device of the invention to the skin, a hypoallergenic adhesive 9 is coated to a lower surface of the support belt 1. The hypoallergenic adhesive 9 can be of pressure sensitive adhesive or acrylate glue.

Figure 2:
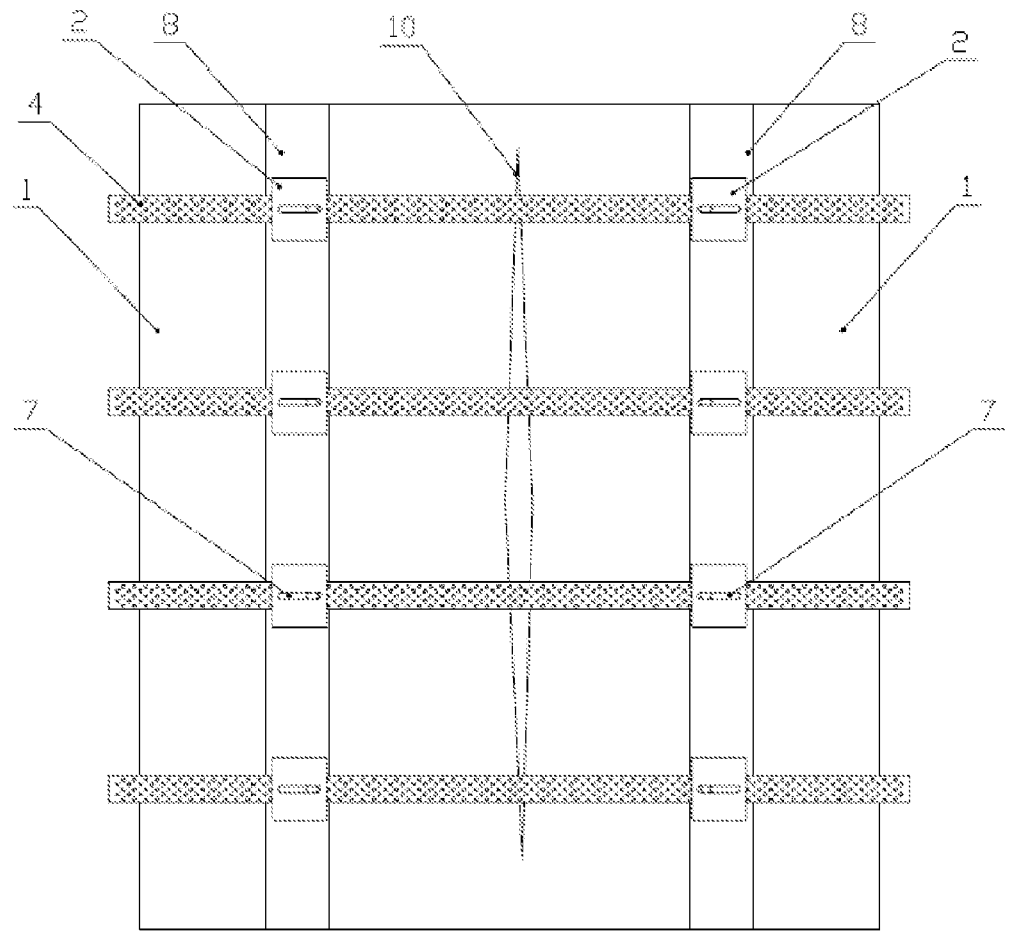
FIG. 2 is a top view of FIG. 1.
Figure 3:
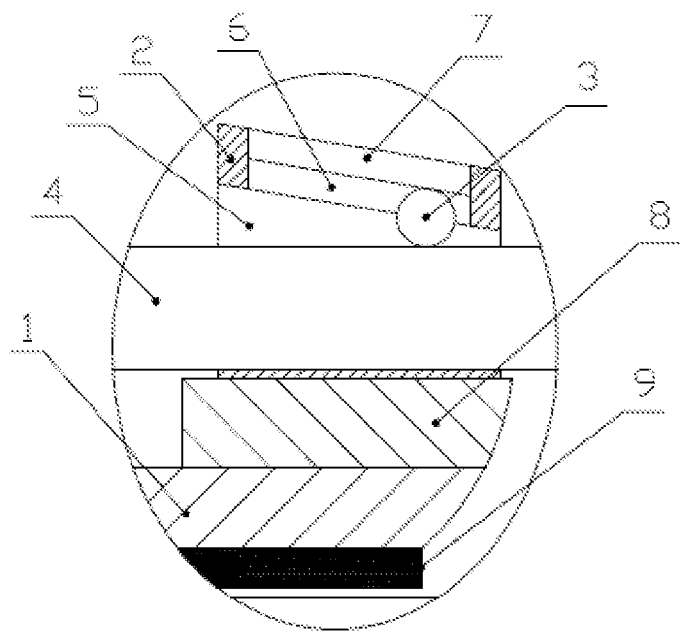
FIG. 3 is a partial enlarged view of position A in FIG. 1.
Figure 4:
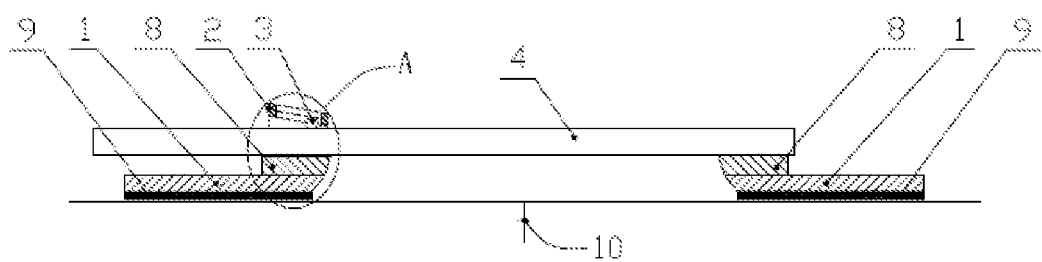
FIG. 4 is a structural diagram of another embodiment of the invention.

Among the embodiments, as one of preferred embodiments, the support structure on each side is provided with the locking buckle 2, and two ends of the locking bar 4 are movably connected with the locking buckle 2 at both sides of the skin wound 10, as shown in FIG. 1 and FIG. 2. In locking the locking bar 4 in the embodiment, the locking member 3 at both sides of the skin wound 10 shall be operated at the same time to lock the locking bar 4. As another preferred embodiment, the locking buckle 2 is only arranged on the support structure at one side of the skin wound 10, one end of the locking bar 4 is movably connected with the locking buckle 2, and the other end thereof is fixedly connected to the support structure at the other side, as shown in FIG. 4. In locking the locking bar 4 in the embodiment, the locking bar 4 can be locked only by the locking member 3 at the side with the locking buckle 2.

The invention claimed is:

1. A skin wound closure device, comprising:
a support structure respectively configured to be arranged at both sides of a skin wound,
at least one locking device being arranged above the support structure, the locking device comprising a locking bar and a locking buckle arranged on the support structure, and the locking bar being movably connected within the locking buckle and having an upper surface,
a locking member arranged adjacent the locking buckle, which can lock or loosely fit the locking bar in the locking buckle,
a through hole arranged in the locking buckle and through which the locking bar passes and is sheathed, and
a chute is arranged at a top wall of the through hole, the chute having an inside top wall and an outside top wall,
wherein the locking member is a rolling element arranged between the upper surface of the locking bar and a top wall of the through hole, the locking member being arranged in the chute and having a diameter at least a height from the inside top wall of the chute to an upper surface of the locking bar, the diameter of the locking member being less than a height from the outside top wall of the chute to the upper surface of the locking bar.

2. The skin wound closure device of claim 1, further comprising a bar through hole arranged on a top of the locking buckle and in communication with the chute.

3. The skin wound closure device of claim 2, wherein a projection for increasing friction force is arranged at the upper surface of the locking bar.

4. The skin wound closure device of claim 3, wherein the support structure respectively configured to be located at both sides of the skin wound comprises a support belt and a base belt arranged on an upper surface of the support belt, and the locking buckle is fixedly arranged on the base belt.

5. The skin wound closure device of claim 4, wherein the base belt is arranged at an inside edge of the upper surface of the support belt, and the support belt and an inside edge of the base belt are of an arcuate surface.

6. The skin wound closure device of claim 5, wherein a hypoallergenic adhesive is coated to a lower surface of the support belt.

7. The skin wound closure device of claim 1, wherein the support structure configured to be at each side of the skin wound is provided with the locking buckle, and two ends of the locking bar are movably connected with the locking buckle at both sides of the skin wound.

8. The skin wound closure device of claim 1, wherein the locking buckle is only configured to be arranged on the support structure at one side of the skin wound, one end of the locking bar is movably connected with the locking buckle, and the other end thereof is fixedly connected to the support structure at the other side of the skin wound.

9. The skin wound closure device of claim 1, wherein the locking buckle and the locking bar are in an automatic locking relationship via the locking member.

10. A skin wound closure device, comprising:
a support structure respectively configured to be arranged at both sides of a skin wound;
at least one locking device being arranged above the support structure, the locking device including a locking bar and a locking buckle arranged on the support structure, the locking bar being movably connected within the locking buckle and having an upper surface, the locking buckle having a top wall;
a locking member arranged on the locking buckle, which can lock or loosely fit the locking bar in the locking buckle; and
a through hole arranged in the locking buckle and through which the locking bar passes and is sheathed, the through hole being defined by the top wall of the locking buckle,
wherein the locking member is a rolling element arranged between the upper surface of the locking bar and the top wall of the locking buckle.

11. The skin wound closure device of claim 10, wherein the rolling element is one of substantially spherical and a rolling column.

12. The skin wound closure device of claim 10, further comprising a chute arranged at the top wall of the locking buckle, wherein the rolling element is arranged in the chute, and a diameter of the rolling element is at least a height from an inside top wall of the chute to the upper surface of the locking bar, and less than a height from an outside top wall of the chute to the upper surface of the locking bar.

13. The skin wound closure device of claim 12, wherein the locking buckle and the locking bar are in an automatic locking relationship via the locking member.

14. The skin wound closure device of claim 12, further comprising a bar through hole arranged on the top wall of the locking buckle and in communication with the chute.

15. The skin wound closure device of claim 14, wherein a projection for increasing friction force is arranged at the upper surface of the locking bar.

16. The skin wound closure device of claim 15, wherein the support structure respectively configured to be located at both sides of the skin wound comprises a support belt and a base belt arranged on an upper surface of the support belt, and the locking buckle is fixedly arranged on the base belt.

17. The skin wound closure device of claim 16, wherein the base belt is arranged at an inside edge of the upper surface of the support belt, and the support belt and an inside edge of the base belt are of an arcuate surface.

18. The skin wound closure device of claim 17, wherein a hypoallergenic adhesive is coated to a lower surface of the support belt.

19. The skin wound closure device of claim 10, wherein the support structure configured to be at each side of the skin wound is provided with the locking buckle, and two ends of the locking bar are movably connected with the locking buckle at both sides of the skin wound.

20. The skin wound closure device of claim 10, wherein the locking buckle is only configured to be arranged on the support structure at one side of the skin wound, one end of the locking bar is movably connected with the locking buckle, and the other end thereof is fixedly connected to the support structure at the other side of the skin wound.

* * * * *